United States Patent

Kisfaludy et al.

[11] 4,021,421
[45] May 3, 1977

[54] BENZODIAZEPINE DERIVATIVES

[75] Inventors: Lajos Kisfaludy; Julianna Röhricht; Laszlo Urögdi; Szabolcs Szeberenyi; Eva Palosi; Laszlo Szporny, all of Budapest, Hungary

[73] Assignee: Richter Gedeon Vegyeszeti Gyar Rt., Budapest, Hungary

[22] Filed: June 23, 1975

[21] Appl. No.: 589,079

[30] Foreign Application Priority Data

June 25, 1974 Hungary .............................. RI 540

[52] U.S. Cl. .......................... 260/239.3 D; 424/244
[51] Int. Cl.² ...................................... C07D 243/24
[58] Field of Search ............................ 260/239.3 D

[56] References Cited

UNITED STATES PATENTS 3,236,838  2/1966  Archer et al. ............. 260/239.3 D

*Primary Examiner*—Henry R. Jiles
*Assistant Examiner*—Robert T. Bond
*Attorney, Agent, or Firm*—Karl F. Ross; Herbert Dubno

[57] ABSTRACT

New benzodiazepine derivatives of the formula (I),

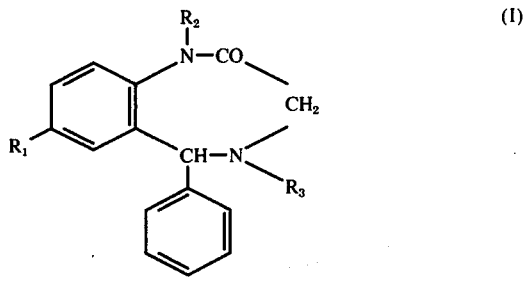

wherein
$R_1$ stands for halogen, trifluoromethyl, nitro or amino,
$R_2$ stands for hydrogen or alkyl, and
$R_3$ stands for nitroso, amino, alkylideneamino, substituted alkylideneamino, aralkylideneamino, substituted aralkylideneamino, acylamido or substituted acylamido.

The new compounds possess remarkable enzyme-inducing effects and exert only moderate central nervous activities.

16 Claims, No Drawings

BENZODIAZEPINE DERIVATIVES

This invention relates to new benzodiazepine derivatives and pharmaceutical compositions containing the same, as well as to a process for the preparation thereof.

More particularly, the invention relates to $N^4$-(substituted)-1,3,4,5-tetrahydro-2H-1,4-benzodiazepine-2-one derivatives of the formula (I),

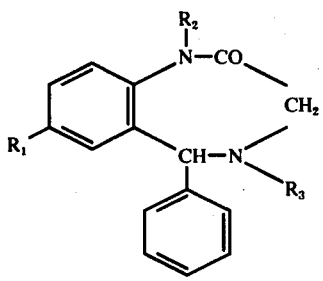

wherein
$R_1$ is halogen, trifluoromethyl, nitro or amino,
$R_2$ is hydrogen or alkyl, and
$R_3$ is nitroso, amino, optionally substituted alkylindeneamino, substituted or unsubstituted aralkylideneamino or substituted or unsubstituted acylamido.

As is known, 1,4-benzodiazepine derivatives attained a great practical importance in the last decade. These compounds possess primarily excellent tranquillo-sedative effects.

Several methods have already been described for the preparation of certain 4-substituted-tetrahydro-1,4-benzodiazepine derivatives, these known compounds differ, however, from those according to the invention in the nature of the substituent attached to position 4.

Thus, according to the French Pat. No. 1,339,762, 1-monosubstituted and 1,4-disubstituted tetrahydrobenzodiazepine derivatives are prepared by the direct alkylation of 1,4-tetrahydro-benzodiazepine (see also J. Med. Chem. 7, 386; 1964).

According to the U.S. Pat. No. 3,507,474 and the Dutch patent application No. 69 16,320 $N^4$-substituted tetrahydro-1,4-benzodiazepine-2-one derivatives are prepared from the appropriate isoquinoline compounds by ring expansion.

The Japanese Pat. No. 48-25,199 describes the preparation of tetrahydro-1,4-benzodiazepine-2-one derivatives having a substituted carbamoyl group in position 4. No data referring to the biological activities of the compounds are disclosed in the cited reference.

In the new compounds according to the invention $R_1$, when halogen can be fluorine, chlorine, bromine or iodine, preferably chlorine.

As alkyl group, $R_2$ can be a straight-chained or branched alkyl group, preferably a lower alkyl group with 1 to 6 carbon atoms. Such groups are e.g. methyl, ethyl, n-propyl, isopropyl, n-butyl, isobutyl, t-butyl, amyl, isoamyl, hexyl, etc. A preferred representative of the alkyl groups is the methyl group.

As alkylideneamino group, $R_3$ can preferably be a lower alkylideneamino group, particularly a straight-chained or branched alkylideneamino group with 2 to 7 carbon atoms. Of these groups e.g. the ethylideneamino, propylideneamino, isopropylideneamino, butylideneamino, isobutylideneamino, t-butylideneamino, amylideneamino, isoamylideneamino, hexylideneamino and heptylideneamino groups are to be mentioned.

The aralkylidene moiety of the aralkylideneamino group mentioned in the definition of $R_3$ can be a mono- or polycyclic aralkylidene group with 7 to 20 carbon atoms in the aromatic and 1 to 6 carbon atoms in the aliphatic part. Of these aralkylidene groups e.g. the benzylidene, phenethylidene, phenylpropylidene, phenylbutylidene, naphthylmethylidene, napthylethylidene, naphthylpropylidene and naphthylbutylidene groups are to be mentioned.

The alkylidene and aralkylidene groups listed above can have one or more identical or different substituents, such as halogen (e.g. chlorine, fluorine, bromine or iodine), hydroxy, trifluoromethyl, nitro, amino, mono- or di-substituted amino (e.g. mono- or di-alkyl-, -aryl- or -acyl-amino), oxo, thio, cyano, sulfo, alkyl, cycloalkyl, alkenyl, cycloalkenyl, aryl, alkoxy, alkenyloxy, aryloxy, alkylthio, etc. The substituents may be attached both to the aromatic and to the aliphatic part of the alkylidene and aralkylidene groups concerned.

Furthermore, $R_3$ can be an acylamido group containing an acyl group derived from an aliphatic or aromatic carboxylic acid.

Of the acyl groups derived from aliphatic carboxylic acids e.g. acyl groups of saturated monocarboxylic acids (such as formic acid, acetic acid, propionic acid, isomeric valeric acids, etc.), furthermore the acyl groups of unsaturated monocarboxylic acids (such as acrylic acid, crotonic acid, vinylacetic acid, methacrylic acid, etc.) are to be mentioned. The hydrocarbyl chain of these acyl groups can contain preferably 1 to 6 carbon atoms, and optionally one or more substituent(s) may be attached to said hydrocarbyl chain. Of these substituents e.g. the halogens (such as fluorine, chlorine, bromine or iodine) attached to the same or different carbon atoms (see e.g. monochloroacetyl, $\alpha$, $\beta$-dibromopropionyl, trifluoroacetyl, $\gamma$-chlorobutyryl, etc.), furthermore the oxo, amino, and aryl (such as phenyl, diphenyl, naphthyl, etc.) groups are to be mentioned.

The aromatic acyl groups may be derived e.g. from benzoic acid, diphenylcarboxylic acids or naphthoic acids. Optionally one or more substituent(s), such as a halogen atom or an alkyl, alkenyl, alkoxy, nitro, amino, hydroxy, trifluoromethyl, cyano, sulfo, thio or oxo group may be attached to the aromatic rings of said acyl groups.

The alkyl groups mentioned among the possible substituents of the alkylideneamino, aralkylideneamino and acylamido groups may be preferably lower alkyl groups with 1 to 6 carbon atoms, such as methyl, ethyl, n-propyl, isopropyl, n-butyl, isobutyl, t-butyl, amyl, isoamyl, etc. groups. Of the alkoxy groups the straight-chained or branched $C_{1-6}$ lower alkoxy groups, such as methoxy, ethoxy, n-propoxy, isopropoxy, n-butoxy, isobutoxy, t-butoxy, amyloxy, isoamyloxy or isomeric hexyloxy groups are the preferred ones. Of the alkenyl groups e.g. the allyl group; of the alkenyloxy groups e.g. the allyloxy group; of the aryl groups e.g. the mono- or polycyclic $C_{6-14}$ aromatic hydrocarbyl groups (such as phenyl, diphenyl or naphthyl group); of the aryloxy groups e.g. the phenoxy, diphenoxy or naphthoxy group; of the aralkyl groups e.g. the $C_{7-20}$ monoor polycyclic groups (such as the benzyl, phenethyl, phenylpropyl, phenylbutyl, naphthylmethyl, naphthylethyl, naphthylpropyl or naphthylbutyl group); of the aralkoxy groups e.g. the benzyloxy, phenethoxy, phenylpropoxy, phenylbutoxy, naphthylmethoxy, naphthylethoxy, napthylpropoxy or naphthylbutoxy group; of the cycloalkyl and cycloalkenyl groups respectively, the mono- or polycyclic, saturated or unsaturated $C_{5-20}$ groups (such as the cyclopentyl, cyclopentenyl, cyclohexyl or cyclohexenyl group); whereas of the acyl groups those groups listed above are to be mentioned. The alkylthio groups may contain e.g. the alkyl groups mentioned above.

A common characteristic of the compounds having the formula (I) is that they contain a direct N—N bond in position 4.

The preferred representatives of the compounds having the formula (I) are those wherein
 $R_1$ is halogen, trifluoromethyl, nitro or amino,
 $R_2$ hydrogen or alkyl, and
 $R_3$ is nitroso group, amino group, benzalamino group having optionally a halogen, nitro or hydroxy substituent, or an acylamino group having optionally one or more substituent(s) (preferably an alkylcarbonylamino group having optionally an amino, aralkoxycarbonylamino or halogen substituent, such as glycylamino, acetylamino or chloroacetylamino).

Particularly preferred are those compounds of the formula (I), wherein
 $R_1$ is halogen,
 $R_2$ is hydrogen or lower alkyl, and
 $R_3$ is a nitroso group, an amino group, a benzalamino group having optionally a halogen (preferably chlorine), nitro or hydroxy substituent, or a $C_{1-6}$ alkylcarbonylamino group having optionally a halogen (preferably chlorine) substituent.

The most preferred representatives of the above compounds are those wherein $R_1$ is chlorine, $R_2$ is hydrogen or methyl, and $R_3$ is nitroso or amino.

The compounds of the formula (I), wherein $R_1$, $R_2$ and $R_3$ each have the same meanings as defined above, can be prepared according to the invention as follows: a 1,3,4,5-tetrahydro-2H-1,4-benzodiazepine-2-one derivative of the formula (II),

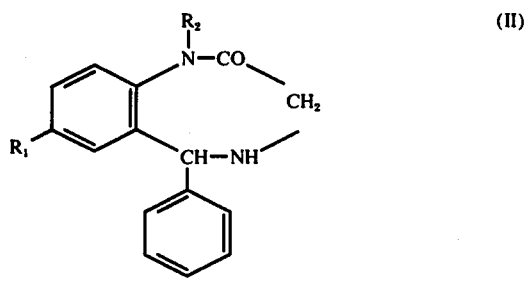

wherein $R_1$ and $R_2$ each have the same meanings as defined above, is subjected to direct nitrosation, and, if desired, the thus obtained $N^4$-nitroso compound of the formula (III),

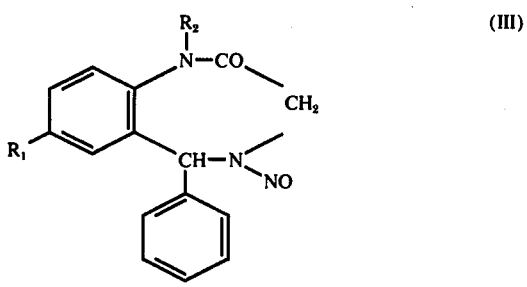

wherein $R_1$ and $R_2$ each have the same meanings as defined above, is reduced, and, if desired, a. the thus-obtained $N^4$-amino compound of the formula (IV),

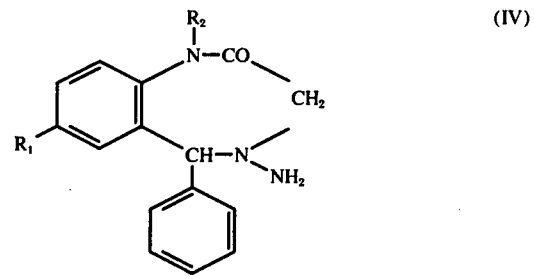

wherein $R_1$ and $R_2$ each have the same meanings as defined above, is reacted with an aldehyde of the formula (V), $$R_4\text{—CHO} \qquad (V)$$

wherein $R_4$ stands for an optionally substituted alkyl, aryl or aralkyl group, or b. the $N^4$-amino compound of the formula (IV), obtained as described above, is reacted with a compound of the formula (VI), $$R_5\text{—CO—Y} \qquad (VI)$$

wherein Y is halogen or hydroxy and $R_5$ is an optionally substituted aliphatic or aromatic hydrocarbyl group, and, if desired, any compound of the formula (I), wherein $R_2$ stands for hydrogen and the other substituents are as defined above, is alkylated.

All compounds prepared by the above process are novel.

The starting substances of the formula (II), wherein $R_1$ and $R_2$ each have the same meanings as defined above, can be prepared e.g. as described in the Hungarian patent specification No. 155,251.

In the compounds of the formula (V) $R_4$ represents a straight-chained or branched alkyl group with preferably 1 to 6 carbon atoms (such as methyl, ethyl, n-propyl, isopropyl, n-butyl, isobutyl, t-butyl, amyl, isoamyl or hexyl group) as alkyl; a $C_{6-14}$ mono- or polycyclic aromatic hydrocarbyl group (such as phenyl, diphenyl or naphthyl group) as aryl; and a mono- or polycyclic $C_{7-20}$ aryl-($C_{1-6}$ alkyl) group (such as benzyl, phenethyl, phenylpropyl, phenylbutyl, naphthylmethyl, naphthylethyl or naphthylbutyl group) as aralkyl.

In the compounds of the formula (VI) $R_5$ may represent a saturated or unsaturated, straight-chained or branched hydrocarbyl group (preferably a $C_{1-6}$ alkyl, alkenyl or alkynyl group) as aliphatic hydrocarbyl; or an aryl group listed in connected with the definition of $R_4$ as aromatic hydrocarbyl. In these compounds Y represents fluorine, chlorine, bromine or iodine as halogen.

The hydrocarbyl groups present in the compounds of the formula (V) or (VI) (such as e.g. the alkyl or aryl groups) may have one or more identical or different substituents. Of the substituents e.g. the following are to be mentioned: halogen atoms (such as chlorine, fluorine, bromine or iodine), hydroxy group, trifluoromethyl group, nitro group, amino group, mono- or disubstituted amino groups (such as mono- or di-alkyl-, -aryl- or -acylamino groups), oxo group, thio group, cyano group, sulfo group, alkyl groups, cycloakyl groups, alkenyl groups, cycloalkenyl groups, aryl groups, alkoxy groups, alkenyloxy groups, aryloxy groups, alkylthio groups, etc. These substituents are identical with the possible substituents of the $R_3$ group.

The direct nitrosation of the compounds having the formula (II) is performed with nitrous acid or with an alkali nitrite (preferably sodium nitrite) in the presence or an acid. As acid preferably a mineral acid, such as a hydrogen halide, sulfuric acid, etc. can be applied. The reaction is performed preferably at lower temperatures, particularly at a temperature of about 0° C, thus the mixture should be cooled during the total reaction time. When an alkali nitrite is used as nitrosating agent, this compound is added in an amount at least equivalent with the amount of the starting substance of the formula (II). In order to ensure a complete reaction and to obtain higher yields it is preferably, however, to use the nitrite reagent in excess, such as in a molar excess.

According to a preferred method of the invention a compound of the formula (II) is suspended in concentrated hydrochloric acid, an aqueous solution of sodium nitrite is added dropwise to the suspension at a temperatures of about 0° C, and when the reaction is over the mixture is rendered alkaline. In this way the respective compounds of the formula (III), wherein $R_1$ and $R_2$ each have the same meanings as defined above, are obtained. The reaction mixture can be alkalinified with any strong basis, such as with an aqueous solution of an alkali hydroxide (e.g. sodium or potassium hydroxide), but it is preferable to use concentrated ammonia for this purpose. The neutralization of the mixture is performed preferably under intense cooling.

If desired, a compound of the formula (III), obtained as described above, can be reduced to yield a compound of the formula (IV), wherein $R_1$ and $R_2$ each have the same meanings as defined above. The reduction is performed in a manner commonly applied to convert a nitroso compound into an amino derivative, using preferably a mild reducing agent. As reducing agent preferably zinc powder is applied in acetic acid medium. According to a preferred method of the invention a $N^4$-nitroso-tetrahydro-1,4-benzodiazepine derivative of the formula (III) is suspended in acetic acid, and zinc powder is added in small portions to the stirred suspension. During this operation the mixture is cooled with water. When the reaction terminates, the mixture is rendered alkaline to separate the obtained product of the formula (IV).

The amino compounds of the formula (IV), obtained as described above, can be converted into their substituted derivatives in two ways, both of them being based on the reactivity of the amino group.

According to process variant a) a $N^4$-amino derivative of the formula (IV), wherein $R_1$ and $R_2$ each have the same meanings as defined above, is reacted with an aldehyde of the formula (V), wherein $R_4$ has the same meanings as defined above. In this way compounds of the formula (I) wherein $R_1$ and $R_2$ each have the same meanings as defined above and $R_3$ is an optionally substituted alkylideneamino or aralkylideneamino group, are obtained.

The compounds of the formula (V) are used preferably in a slight excess, e.g. in an amount of 1.1 to 1.8 (preferably 1.3 to 1.5 moles per one mole of the starting substance. The reaction is performed in an organic solvent inert towards the reaction, preferably in an aromatic hydrocarbon, such as in benzene or toluene. If desired, a minor amount of an acid, such as formic acid or p-toluenesulfonic acid, can also be added to the reaction mixture, but the reaction proceeds with satisfactory results even in the absence of an acid catalyst. The time and temperature of the reaction are not critical, but it is preferable to perform the reaction at about room temperature. Under these conditions the reaction proceeds generally within 5 to 24 hours.

According to a preferred method of process variant a) a $N^4$-amino-tetrahydro-1,4-benzodiazepine derivative of the formula (IV) is dissolved in an inert organic solvent, such as in benzene, an aldehyde of the formula (V), wherein $R_4$ has the same meanings as defined above, is added to the solution, and the mixture is stirred at room temperature overnight.

According to process variant b) a $N^4$-amino compound of the formula (IV), wherein $R_1$ and $R_2$ each have the same meanings as defined above, is reacted with a compound of the formula (VI), wherein $R_5$ and Y each have the same meanings as defined above, to obtain a $N^4$-substituted compound of the formula (I), wherein $R_1$ and $R_2$ each have the same meanings as defined above and $R_3$ is an optionally substituted acylamido group.

If a compound of the formula (VI), wherein Y stands for hydroxy, is used as starting substance, a conventional condensing agent, such as dicyclohexyl carbodiimide, can be added to the mixture in order to accelerate or complete the reaction.

The starting substances are used preferably in approximately equimolar amounts. The condensing agent can be added preferably in an excess of 5 to 15%.

If a compound of the formula (VI), wherein Y is halogen, is used as acylating agent, a conventional acid binding agent, such as a tertiary organic base or an inorganic base (e.g. an alkaline earth metal oxide, such as magnesium oxide) can be added to the mixture in order to accelerate or complete the reaction.

If, however, the individual components are sufficiently reactive, both of the above-discussed reactions proceed with an appropriate rate even without using a condensing or acid binding agent, respectively.

Any reaction of process variant (b) is performed in a solvent inert towards the reaction, such as in an alkyl carboxylate (e.g. ethyl acetate), a chlorinated hydrocarbon (e.g. chloroform), etc. The time and temperature of the reaction are not critical, but it is preferable to perform the reaction at about room temperature. Under such conditions the reaction proceeds within about 5 to 24 hours.

If any of the reactants having the formula (V) or (VI) contains an amino substituent, a conventional protecting group is attached to the amino group prior to performing the reaction. Of the applicable protecting groups e.g. the urethane-type protecting groups (such as t-butoxycarbonyl or an optionally substituted benzyloxycarbonyl group) are to be mentioned. In this event the reaction yields a compound of the formula (I), wherein $R_1$ and $R_2$ each have the same meanings as defined above, and $R_3$ is a group containing a protected amino substituent. The free amino derivatives can be obtained by removing the protecting groups.

The protecting groups can be split off easily by solvolysis or hydrogenolysis. The solvolytically removable protecting groups (e.g. acyl groups) are split off e.g. with a dilute acid, preferably hydrobromic acid in glacial acetic acid. The hydrogenolytically removable protecting groups are split off preferably by catalytic hydrogenation using a conventional hydrogenating catalyst, preferably a palladium catalyst. This reaction is performed in a solvent or suspending agent, optionally under superatmospheric pressure. As solvent or suspending agent e.g. water, a lower aliphatic alcohol, a cyclic ether such as dioxane or tetrahydrofuran, an aliphatic ether, dimethyl formamide, etc., or the mixtures thereof can be applied.

Any of the compounds having the formula (I), wherein $R_1$ and $R_3$ each have the same meanings as defined above and $R_2$ stands for hydrogen, can be alkylated, if desired, to obtain the respective $R_2$ = alkyl derivatives. In this reaction conventional alkylating agents, such as alkyl halides (preferably alkyl iodides) or dialkyl sulfates can be used.

One may proceed e.g. by converting first a compound of the formula (I) into its alkali metal derivative, and reacting the thus-obtained alkali metal compound with an appropriate alkylating agent. The alkali metal compound can be prepared e.g. by reacting the appropriate compound of the formula (I), wherein $R_2$ is hydrogen and $R_1$ and $R_3$ each have the same meanings as defined above, with an alkali metal, alkali hydride or alkali amide, particularly with sodium or with a sodium compound, at 0° to 150° C in an inert solvent, such as dioxane, dimethyl formamide, benzene or toluene.

The reaction mixtures can be processed by methods known in the art. The actual method of processing depends on the nature of the starting substance, the end-product and the solvent. When the product separates from the reaction mixture it is simply filtered off, whereas when the product remains in solution, the product can be precipitated with an appropriate solvent or the solution can be evaporated optionally after the removal of the solid by-products.

When processing the reaction mixture the product is obtained generally in crystalline form. If, however, an oily substance is obtained, this can be crystallized generally very easily using conventional solvents, e.g. aliphatic or cyclic ethers, such as diethyl ether, dioxane, tetrahydrofuran, etc.

If necessary, the compounds of the formula (I), wherein $R_1$, $R_2$ and $R_3$ each have the same meanings as defined above, can be subjected to additional purification steps, such as recrystallization. As recrystallization solvent e.g. an aliphatic alcohol, such as methanol or ethanol, an aromatic hydrocarbon, such as benzene, a ketone, such as acetone, an aliphatic ester, particularly an alkanecarboxylate such as ethyl acetate, an aliphatic hydrocarbon, particularly a $C_{5-10}$ saturated aliphatic hydrocarbon such as n-hexane, an ether, particularly a dialkyl ether such as diethyl ether, a saturated cyclic ether, such as tetrahydrofuran, furthermore acetonitrile, as well as the mixtures thereof (e.g. a mixture of tetrahydrofuran and hexane or a mixture of ethyl acetate and ether) can be used.

The process according to the invention provides the compounds of the formula (I) with high yields and in easily identifiable estate. The elementary analysis data of the obtained substances are in good agreement with the calculated values.

The new tetrahydro-1,4-benzodiazepine derivatives of the formula (I) possess remarkable enzyme-inducing effects and exert only moderate central nervous activities.

In the pharmacological studies performed in the last decade numerous compounds, among them several known medicaments too, proved to exert an inducing effect on the mixed-function oxidase system bound to the endoplasm reticulum of the liver. No correlation was found so far between the enzyme-inducing effects and the chemical structures of the compounds concerned. The primary function of the above enzyme system is to inactivate and eliminate the xenobiotic substances, but it also controls the metabolism of endogeneous substances, such as steroide hormones. The induction of the enzyme system is bound to the acceleration of the metabolism of the substances in question. The enzyme inducing compounds attain a steadily expanding use in the therapy primarily for the treatment of diseases connected with the overproduction of certain steroide hormones and for hyperbilirubinaemic states connected with conjugation disorders.

The enzyme-inducing effects of the new compounds were examined under in vivo conditions by determining the hexobarbital oxidase activity. The active agents of the formula (I) were administered to male Wistar rats weighing 50 to 60 g. in oral dosages of 40 mg./kg. The effect appears 24 hours after the administration of the enzyme-inducing substance. At that time the inactivation rate of hexobarbital was determined by administering intravenously 40 mg./kg. of hexabarbital sodium into the animals and measuring the time elapsed between the administration and the reappearance of the righting reflex. The period of sleep observed for the animals treated with the new compounds was compared to that observed in the control group (the animals belonging to the control group were treated with carrier substance only).

24 Hours after the administration of the enzyme-inducing compounds the in vivo inactivation of hexobarbital accelerates, which is evidenced by the shortening of the period of sleep. The results were expressed as percentage differences with respect to the controls. On the basis of the preliminary experiments a difference greater than 25% was regarded to be biologically significant. The results of this test are summarized in Table 1.

Table 1

| Substance (Example No.) | Dosage mg./kg. | Period of sleep, min. ± standard error | Difference % |
|---|---|---|---|
| Control | — | 28.50 ± 3.12 | — |
| 2 | 40 | 13.97 ± 2.10 | −51 |
| 1 | 40 | 16.53 ± 1.93 | −42 |
| 3 | 40 | 18.57 ± 2.06 | −35 |
| 5 | 40 | 11.96 ± 1.38 | −58 |
| 10 | 40 | 16.82 ± 1.84 | −41 |
| 13 | 40 | 20.24 ± 2.17 | −29 |
| 12 | 40 | 19.10 ± 2.28 | −33 |

The biological half life-time of hexobarbital was determined by subjecting the plasm to UV spectrophotometry. The results of this test performed with the compound prepared according to Example 5 (the most active representative of the new compounds according to the invention) are summarized in Table 2. From the data of Table 2 it is clear that the compound prepared according to Example 5 effectively decreases the half life-time of hexobarbital in rats.

Table 2

| Substance | $T_{1/2}$, min. |
|---|---|
| Control | 38 |
| Example 5 | 26 |

The compounds of the formula (I), wherein $R_1$, $R_2$ and $R_5$ each have the same meanings as defined above, can be converted into orally, parenterally or enterally administerable pharmaceutical compositions using conventional non-toxic, inert solid or liquid carriers and/or auxiliary substances. The pharmaceutical compositions may contain one or more compound(s) of the formula (I), or they may contain the compounds of the formula (I) in combination with other pharmaceutically active substances. As carrier, e.g. water, gelatine, lactose, starch, pectin, magnesium stearate, stearic acid, talc, vegetable oils (such as peanut oil, olive oil, etc.), gum arabic, polyalkylene glycols, vazeline, etc. can be applied. The active agents can be formulated to obtain solid compositions (e.g. tablets, lozenges, dragees, capsules, pills, etc.) or liquid preparations (e.g. oily or aqueous solutions, suspensions, emulsions, syrups, soft gelatine capsules, injectable aqueous or oily solutions or suspensions, etc.). The amount of the solid carrier substance may vary within wide limits; a single dosage unit contains preferably about 0.025 to 1 g. of solid carrier. The compositions may contain optionally usual pharmaceutical auxiliary agents, such as preservatives, stabilizing agents, wetting agents, emulsifying agents, salts for adjusting the osmotic pressure, buffers, flavoring agents, aroma substances, etc.

The pharmaceutical compositions can be prepared by the usual phramaceutical procedures, including e.g. screening, mixing, granulation, pressing and/or dissolution. If necessary, the compositions can be subjected to further pharmaceutical processing steps (e.g. sterilization).

The invention is elucidated in the following non-limiting Examples.

The degrss of purity of the produced substances were determined by thin layer chromatography. The $R_f$ values were determined on a Stahl C silica gel plate (Merck), using as eluant one of the following systems: (1) 1:1:8 mixture of n-hexane, acetic acid and chloroform; (2) 95:5 mixture of benzene and methanol; (3) 75:20:5 mixture of chloroform, methanol and acetic acid; (4) 1:4:8 mixture of n-hexane, ethyl acetate and chloroform; (5) 4:1:1 mixture of n-butanol, acetic acid and water. The spots were developed by the chlorine-tolidine technique. The melting points were determined in a dr. Tottoli type apparatus (the melting points given in the Examples are non-corrected values). In some instances the structures of the products were identified by IR or MNR spectroscopy or by mass spectrometry.

EXAMPLE 1

1-Methyl-4-nitroso-5-phenyl-7-chloro-1,3,4,5-tetrahydro-2H-1,4-benzodiazepine-2-one 16.0 g. (55.6 mmoles) of 1-methyl-5-phenyl-7-chloro-1,3,4,5-tetrahydro-2H-1,4-benzodiazepine-2-one are suspended in 56 ml. of concentrated hydrochloric acid. The suspension is cooled to 0° C, and a solution of 3.9 g. (55.6 mmoles) of sodium nitrite in 20 ml. of water is added dropwise. The mixture is stirred at 0° C for 2 hours, thereafter further 3.9 g. (55.6 mmoles) of sodium nitrite are added as described above. When the reaction terminates the suspension is neutralized with concentrated aqueous ammonia. The alkaline solution is added cautiously, under intense cooling. The separated crude product is filtered off, washed with water, and recrystallized from ethanol. 15.6 g. (88.6%) of 1-methyl-4-nitroso-5-phenyl-7-chloro-1,3,4,5-tetrahydro-2H-benzodiazepine-2-one are obtained; m.p.: 180°-182° C, $R_f^{(1)} = 0.8$.

Analysis: Calculated for $C_{16}H_{14}O_2N_3Cl$ (M = 315.76): C: 60.8%, H: 4.5%, N: 13.3%. Found: C: 60.8%, H: 4.7%, N: 13.3%.

Similarly the following compound can be prepared from the appropriate starting substances:

EXAMPLE 2

4-Nitroso-5-phenyl-7-nitro-1,3,4,5-tetrahyro-2H-1,4-benzodiazepine-2-one

Yield: 80.5%, Melting point: 211°-212° C (after recrystallization from ethanol). $R_f^{(1)} = 0.75$.

Analysis: Calculated for $C_{15}H_{12}N_4O_4$ (M = 312.29): C: 57.7%, H: 3.9%, N: 17.95%. Found: C: 57.6%, H: 4.4%, N: 17.95%.

EXAMPLE 3

1-Methyl-4-amino-5-phenyl-7-chloro-1,3,4,5-tetrahydro-2H-1,4-benzodiazepine-2-one 30 g. of zinc powder are added to a suspension of 9.0 g. (28.4 mmoles) of 1-methyl-4-nitroso-5-phenyl-7-chloro-1,3,4,5-tetrahydro-2H-1,4-benzodiazepine-2-one in 60 ml. of acetic acid under cooling with water and stirring. During the addition the solid dissolves gradually. After 15 minutes of stirring the zinc powder is filtered off, and the filtrate is neutralized with saturated aqueous sodium hydrocarbonate solution. The separated substance, which is difficult to filtrate, is extracted with several portions of chloroform. The chloroform solution is dried and evaporated to a final volume of about 16 ml. 30 ml. of 2 n hydrochloric acid are added to the concentrate, and the mixture is allowed to stand for some minutes. The separated impurities are filtered off, and the obtained two-phase filtrate is neutralized with a saturated aqueous solution of sodium hydrocarbonate. The chloroform phase is separated, and the aqueous phase is extracted with 2×100 ml. of chloroform. The organic phases are combined, dried, and evaporated to dryness under reduced pressure. The oily residue is crystallized from isopropanol to yield 5.1 g. (59.3 %) of 1-methyl-4-amino-5-phenyl-7-chloro-1,3,4,5-tetrahydro-2H-1,4-benzodiazepine-2-one. M.p.: 147°-148° C; $R_f^{(2)} = 0.15$.

Analysis: Calculated for $C_{16}H_{16}ON_3Cl$ (M = 301.79): C: 63.6%, H: 5.3%, N: 13.9%. Found: C: 63.7%, H: 5.6%, N: 14.3%.

Similarly can be prepared the following compound from the appropriate starting substances:

EXAMPLE 4

4,7-Diamino-5-phenyl-1,3,4,5-tetrahydro-2H-1,4-benzodiazepine-2-one

Yield: 56.6%. M.p: 218°-221° C (after recrystallization from acetonitrile). $R_f^{(3)} = 0.4$.

Analysis: Calculated for $C_{15}H_{16}ON_4$ (M = 268.33): C: 67.1%, H: 6.0%, N: 20.9%. Found: C: 66.8%, H: 6.3%, N: 20.5%.

EXAMPLE 5

1-Methyl-4-benzalamino-5-phenyl-7-chloro-1,3,4,5-tetrahydro-2H-1,4-benzodiazepine-2-one 1 ml. (9.1 mmoles) of benzaldehyde is added to a solution of 2.0 g. (6.6 mmoles) of 1-methyl-4-amino-5-phenyl-7-chloro-1,3,4,5-tetrahydro-2H-1,4-benzodiazepine-2-one in 20 ml. of benzene, and the mixture is stirred at room temperature overnight. At the end of the reaction the mixture is evaporated to dryness under reduced pressure, the residue is triturated with 20 ml. of ether, and the solid substance is filtered off. 2.1 g. (80.7%) of 1-methyl-4-benzalamino-5-phenyl-7-chloro-1,3,4,5-tetrahydro-2H-1,4-benzodiazepine-2-one are obtained. M.p.: 157°–158° C (after recrystallizaton from ethanol). $R_f^{(4)} = 0.7$.

Analysis: Calculated for $C_{23}H_{19}ON_3Cl$ (M = 389.89): C: 70.8%, H: 5.2%, N: 10.8%. Found: C: 70.8%, H: 5.35%, N: 10.4%.

Similarly can be prepared the following compounds from the appropriate starting substances:

EXAMPLE 6

1-Methyl-4-(o-chloro-benzalamino)-5-phenyl-7-chloro-1,3,4,5-tetrahydro-2H-1,4-benzodiazepine-2-one Yield: 91.2%. M.p.: 185°–187° C (after recrystallization from ethanol). $R_f^{(4)} = 0.7$.

Analysis: Calculated for $C_{23}H_{19}ON_3Cl_2$ (M = 424.34): C: 65.1%, H: 4.5%, N: 9.9%. Found: C: 65.0%, H: 4.9%, N: 9.8%.

EXAMPLE 7

1-Methyl-4-(n-nitro-benzalamino)-5-phenyl-7-chloro-1,3,4,5-tetrahydro-2H-1,4-benzodiazepine-2-one Yield: 87.9%. M.p.: 202°–204° C (after recrystallization from ethanol). $R_f^{(4)} = 0.65$.

Analysis:
Calculated for $C_{23}H_{19}O_3N_4Cl$ (M = 434.89): C: 63.6%, H: 4.4%, N: 12.75%. Found: C: 63.3%, H: 4.4%, N: 12.3 %.

EXAMPLE 8

1-Methyl-4-(m-nitro-benzalamino)-5-phenyl-7-chloro-1,3,4,5-tetrahydro-2H-1,4-benzodiazepine-2-one Yield: 93.5 %, M.p.: 224°–226° C (after recrystallization from ethanol). $R_f^{(4)} = 0.65$.

Analysis: Calculated for $C_{23}H_{19}O_3N_4Cl$ (M = 434.89): C: 63.6%, H: 4.4%, N: 12.75%. Found: C: 63.4%, H: 4.4%, N: 12.6%.

EXAMPLE 9

1-Methyl-4-(o-nitro-benzalamino)-5-phenyl-7-chloro-1,3,4,5-tetrahydro-2H-1,4-benzodiazepine-2-one Yield: 90.2%, M.p.: 187°–188° C (after recrystallization from ethanol). $R_f^{(4)} = 0.7$.

Analysis: Calculated for $C_{23}H_{19}O_3N_4Cl$ (M = 434.89): C: 63.6%, H: 4.4%, N: 12.75%. Found: C: 63.6%, H: 4.7%, N: 12.2%.

EXAMPLE 10

1-Methyl-4-(p-hydroxy-benzalamino)-5-phenyl-7-chloro-1,3,4,52H-1,4-benzodiazepine-2-one Yield: 89.5%. M.p.: 135°–137° C (after recrystallization from benzene). $R_f^{(4)} = 0.5$.

Analysis: Calculated for $C_{23}H_{20}O_2N_3Cl$ (M = 405.89): C: 68.05%, H: 4.95%, N: 10.3%. Found: C: 68.3%, H: 5.0%, N: 10.2%.

EXAMPLE 11

1-Methyl-4-glycylamino-5-phenyl-7-chloro-1,3,4,5-tetrahydro-2H-1,4-benzodiazepine-2-one 4.2 g. (0.02 moles) of benzyloxycarbonyl-glycine and 4.0 g. (0.02 moles) of dicyclohexyl carbodiimide are added to a solution of 6.0 g. (0.02 moles) of 1-methyl-4-amino-5-phenyl-7-chloro-1,3,4,5-tetrahydro-2H-1,4-benzodiazepine-2-one in 200 ml. of ethyl acetate. The reaction mixture is stirred at room temperature overnight, thereafter the separated dicyclohexyl urea is filtered off, and the filtrate is evaporated under reduced pressure. The residue is admixed with acetonitrile, the solution is boiled, the separated dicyclohexyl urea is filtered off from the hot solution, and the filtrate is allowed to cool. The separated crude product is filtered off, and crystallized from ethanol. 7.1 g. (72%) of 1-methyl-4-(N-benzyloxycarbonyl-glycylamino)-5-phenyl-7-chloro-1,3,4,5-tetrahydro-2H-1,4-benzodiazepine-2-one are obtained; m.p.: 184°–190° C; $R_f^{(1)} = 0.3$.

Analysis: Calculated for $C_{26}H_{25}O_4N_4Cl$ (M = 492.95): C: 63.3%, H: 5.1%, N: 11.4%. Found: C: 63.6%, H: 4.8%, N: 11.4%.

A mixture of 4.6 g. (9.35 mmoles) of the above product and 25 ml. of 3 n hydrobromic acid in glacial acetic acid is stirred for 0.5 hours under exclusion of air, thereafter 100 ml. of dry ether are added to the solution. The separated substance is filtered off and washed with dry ether. The thus-obtained 4.78 g. of 1-methyl-4-glycylamino-5-phenyl-7-chloro-1,3,4,5-tetrahydro-2H-1,4-benzodiazepine-2-one hydrobromide are suspended in 20 ml. of water, and the pH of the mixture is adjusted to 9 to 10 with concentrated aqueous ammonia. The aqueous suspension is saturated with sodium chloride and extracted with 3×100 ml. of chloroform. The chloroform solution is dried, evaporated to dryness under reduced pressure, and the residue is recrystallized from ethyl acetate. 2.6 g. (76.4%) of 1-methyl-4-glycylamino-5-phenyl-7-chloro-1,3,4,5-tetrahydro-2H-1,4-benzodiazepine-2-one are obtained. M.p.: 173°–175° C; $R_f^{(5)} = 0.35$.

Analysis: Calculated for $C_{18}H_{19}O_2N_4Cl$ (M = 358.82): C: 60.2%, H: 5.3 %, N: 15.6%. Found: C: 60.1%, H: 5.6%, N: 15.6%.

EXAMPLE 12

1-Methyl-4-chloroacetamino-5-phenyl-7-chloro-1,3,4,5-tetrahydro-2H-1,4-benzodiazepine-2-one 3. g. of magnesium oxide are added to a solution of 3.0 g. (0.01 mole) of 1-methyl-4-amino-5-phenyl-7-chloro-1,3,4,5-tetrahydro-1,4-benzodiazepine-2-one in 30 ml. of chloroform, and a solution of 0.82 ml. of chloroacetyl chloride in 4 ml. of chloroform is added dropwise to the stirred mixture. After 2 hours of stirring a solution of 0.3 ml. of chloroacetyl chloride in 2 ml. of chloroform is added, and the mixture is stirred at room temperature overnight. The magnesium salt is filtered off and washed with chloroform. The filtrate and the wash are combined, washed with 20 ml. of water, dried, and the solvent is evaporated. 3.5 g. (92.5%) of a white, crystalline residue are obtained; m.p.: 226°–228° C. This crude product is recrystallized from acetonitrile to yield purified 1-methyl-4- chloroacetylamino-5-phenyl-7-chloro-1,3,4,5-tetrahydro-2H-1,4-benzodiazepine-2-one; m.p.: 227°–229° C, $R_f^{(1)} = 0.3$.

Analysis:

Calculated for $C_{18}H_{17}O_2N_3Cl$ (M = 378.25): C: 57.2%, H: 4.5%, N: 11.1%. Found: C: 57.1%, H: 4.4%, N: 11.2%.

Similarly the following compound can be prepared from the appropriate starting substances:

EXAMPLE 13

1-Methyl-4-acetylamino-5-phenyl-7-chloro-1,3,4,5-tetrahydro-2H-1,4-benzodiazepine-2-one Yield: 74.5%. M.p.: 198°–206° C (after recrystallizaton from acetonitrile). $R_f^{(1)} = 0.25$.

Analysis: Calculated for $C_{18}H_{18}O_2N_3Cl$ (M = 343.81): C: 62.9%, H: 5.3%, N: 12.2%. Found: C: 62.5%, H: 4.6%, N: 11.65%.

What we claim is:

1. A compound of the formula:

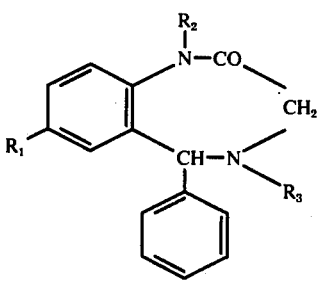

wherein $R_1$ is halogen, trifluoromethyl, nitro or amino;
$R_2$ is hydrogen or $C_1$ to $C_6$ alkyl; and
$R_3$ is nitroso,
  amino,
  $C_2$ to $C_7$ alkylidenamino,
  aralkylidenamino wherein the aryl is $C_7$ to $C_{20}$ and the alkkylidenamino is $C_1$ to $C_6$,
  $C_2$ to $C_7$ alkylidenamino or aralkylidenamino wherein the aryl is $C_7$ to $C_{20}$ and the alkylidenamino is $C_1$ to $C_6$ substituted by at least one halogen, hydroxy, trifluoromethyl, nitro, amino, oxo, thio, cyano, sulfo, $C_1$ to $C_6$ alkyl, $C_5$ to $C_{20}$ cycloalkyl, $C_5$ to $C_{20}$ cycloalkenyl, $C_6$ to $C_{14}$ aryl, $C_1$ to $C_6$ alkoxy, $C_7$ to $C_{20}$ aralkyl, allyl, allyloxy, aryloxy selected from the group which consists of phenoxy, naphthoxy, and diphenoxy; and aralkoxy selected from the group which consists of benzyloxy, phenethoxy, phenylpropxy, phenylbutoxy, naphthylmethoxy, naphthylethoxy, naphthylpropoxy and naphthylbutoxy,
  acylamino wherein the acyl is the acyl group of a carboxylic acid and is $C_1$ to $C_6$ aliphatic, $C_7$ to $C_{20}$ aromatic or
  substituted acylamino wherein the acyl is the acyl group of a carboxylic acid and is $C_1$ to $C_6$ aliphatic or $C_7$ to $C_{20}$ aromatic containing at least one halogen, $C_1$ to $C_6$ alkyl, allyl, $C_1$ to $C_6$ alkoxy, $C_5$ to $C_{20}$ cycloalkyl, nitro, amino hydroxy, trifluoromethyl, cyano, sulfo, thio or oxo.

2. A compound as claimed in claim 1, wherein $R_1$ is halogen, $R_2$ is lower akyl and $R_3$ is nitroso.

3. A compound as claimed in claim 1, wherein $R_1$ is halogen, $R_2$ is lower alkyl and $R_3$ is amino.

4. A compound as claimed in claim 1, wherein $R_1$ is halogen, $R_2$ is lower alkyl and $R_3$ is aralkylideneamino with $C_7$ to $C_{20}$ aryl and $C_1$ to $C_6$ alkyl.

5. The compound defined in claim 1 wherein $R_1$ is halogen, $R_2$ is lower alkyl and $R_3$ is aralkylidenamino wherein the aryl is $C_7$ to $C_{20}$ and the alkylideneamino is $C_1$ to $C_6$ and substituted by at least one halogen, hydroxy, trifluoromethyl, nitro, amino, oxo, thio, cyano, sulfo, $C_1$ to $C_6$ alkyl, $C_5$ to $C_{20}$ cycloalkyl, $C_5$ to $C_{20}$ cycloalkenyl, $C_6$ to $C_{14}$ aryl, $C_1$ to $C_6$ alkoxy, $C_7$ to $C_{20}$ aralkyl, allyl, allyloxy, arlyoxy selected from the group which consists of phenoxy, naphthoxy, and diphenoxy; and aralkoxy selected from the group which consists of benzyloxy, phenethoxy, phenylpropoxy, phenylbutoxy, naphthylmethoxy, naphthylethoxy, naphthylpropoxy and naphthylbutoxy.

6. A compound as claimed in claim 1, wherein $R_1$ is halogen and $R_3$ is acylamino wherein the acyl is a $C_1$ to $C_6$ residue of an aliphatic carboxylic acid or a $C_7$ to $C_{20}$ residue of an aromatic carboxylic acid.

7. The compound defined in claim 1 wherein $R_1$ is halogen, $R_2$ is lower alkyl and $R_3$ is acylamino wherein the acyl is the acyl group of a carboxylic acid and is either $C_1$ to $C_6$ aliphatic, $C_7$ to $C_{20}$ aromatic or substituted acylamino wherein the acyl is the acyl group of a carboxylic acid and is $C_1$ to $C_6$ aliphatic or $C_7$ to $C_{20}$ aromatic wherein either is substituted by at least one halogen, $C_1$ to $C_6$ alkyl, allyl, $C_1$ to $C_6$ alkoxy, nitro, amino, hydroxy, trifluoromethyl, cyano, sulfo, thio, oxo or $C_5$ to $C_{20}$ cycloalkyl.

8. A compound as claimed in claim 1, wherein $R_1$ is halogen, $R_2$ is lower alkyl and $R_3$ is a lower alkanoylamino group.

9. A compound as claimed in claim 1, wherein $R_1$ is halogen, $R_2$ is lower alkyl and $R_3$ is a lower alkanoylamino group substituted by at least one halogen.

10. 1-Methyl-4-nitroso-5-phenyl-7-chloro-1,3,4,5-tetrahydro-2H-1,4-benzodiazepine-2-one, as defined in claim 1.

11. 4-Nitroso-5-phenyl-7-nitro-1,3,4,5-tetrahydro-2H-1,4-benzodiazepine-2-one, as defined in claim 1.

12. 1-Methyl-4-amino-5-phenyl-7-chloro-1,3,4,5-tetrahydro-2H-1,4-benzodiazepine-2-one, as defined in claim 1.

13. 1-Methyl-4-benzalamino-5-phenyl-7-chloro-1,3,4,5-tetrahydro-2H-1,4-benzodiazepine-2-one, as defined in claim 1.

14. 1-Methyl-4-(p-hydroxy-benzalamino)-5-phenyl-7-chloro-1,3,4,5-tetrahydro-2-H-1,4-benzodiazepine-2-one, as defined in claim 1.

15. 1-Methyl-4-chloroacetamino-5-phenyl-7-chloro-1,3,4,5-tetrahydro-2H-1,4-benzodiazepine-2-one, as defined in claim 1.

16. 1-Methyl-4-acetylamino-5-phenyl-7-chloro-1,3,4,5-tetrahydro-2H-1,4-benzodiazepine-2-one, as defined in claim 1.

* * * * *